United States Patent [19]
Walker et al.

[11] Patent Number: 5,443,453
[45] Date of Patent: Aug. 22, 1995

[54] STOP-COCK VALVE

[75] Inventors: Clarence L. Walker, Webster Groves; Frederick F. Schweitzer, Jr., Glencoe; Alfredo E. Patag, St. Louis; Gerald J. Garvey, II, Maryland Heights, all of Mo.

[73] Assignee: Sherwood Medical Company, St. Louis, Mo.

[21] Appl. No.: 230,657

[22] Filed: Apr. 21, 1994

[51] Int. Cl.6 ............................................. A61M 5/00
[52] U.S. Cl. ................................... 604/248; 604/32; 128/766; 137/625.41
[58] Field of Search ................ 128/766; 137/625.41, 137/625.47; 604/30, 32, 248, 280, 283

[56] References Cited

U.S. PATENT DOCUMENTS

| 992,502 | 5/1911 | Hollis . | |
|---|---|---|---|
| 1,162,935 | 12/1915 | Lange . | |
| 3,048,192 | 8/1962 | Murphy, Jr. | 604/248 |
| 3,091,239 | 5/1963 | Moeller . | |
| 3,097,585 | 7/1963 | Carlson | 95/89 |
| 3,536,451 | 10/1970 | Ludwin . | |
| 3,678,960 | 7/1972 | Leibinsohn | 604/248 |
| 3,788,599 | 1/1974 | Cloyd . | |
| 3,831,625 | 8/1974 | Roediger | 137/377 |
| 3,834,372 | 9/1974 | Turney | 604/248 |
| 3,858,601 | 1/1975 | Ensinger | 137/374 |
| 3,957,082 | 5/1976 | Fuson et al. | 604/248 |
| 3,985,133 | 10/1976 | Jenkins et al. . | |
| 3,994,294 | 11/1976 | Knute . | |
| 4,219,021 | 8/1980 | Fink . | |
| 4,460,358 | 7/1984 | Somerville et al. | 604/250 |
| 4,552,334 | 11/1985 | Tomiyama et al. . | |
| 4,557,725 | 12/1985 | Heyne et al. | 604/151 |
| 4,585,411 | 4/1986 | Bocci et al. | 604/245 |
| 4,585,442 | 4/1986 | Mannes | 604/250 |
| 4,593,717 | 6/1986 | Levasseur | 137/625.47 |
| 4,604,093 | 8/1986 | Brown et al. . | |
| 4,689,043 | 8/1987 | Bisha | 604/250 |
| 4,691,895 | 9/1987 | Garff . | |
| 4,904,245 | 2/1990 | Chen et al. | 604/248 |
| 5,005,604 | 4/1991 | Asianian | 604/32 |
| 5,017,192 | 5/1991 | Dodge et al. | 604/250 |
| 5,104,387 | 4/1992 | Pokomey et al. . | |
| 5,156,186 | 10/1992 | Manska | 137/556 |
| 5,219,327 | 6/1993 | Okada | 604/34 |
| 5,244,463 | 9/1993 | Cordner, Jr. et al. | 604/151 |
| 5,364,364 | 11/1994 | Kasvikis et al. | 604/151 |

FOREIGN PATENT DOCUMENTS

| 45910 | 7/1932 | Denmark . |
|---|---|---|
| 576400 | 5/1958 | Italy . |
| 62744 | 1/1913 | Sweden . |

Primary Examiner—C. Fred Rosenbaum
Assistant Examiner—Perry E. Van Over
Attorney, Agent, or Firm—Andrew J. Beck; Montgomery W. Smith; Gene B. Kartchner

[57] ABSTRACT

The present invention relates to a stop-cock valve useable in conjunction with a fluid delivery set for delivering fluids such as intravenous fluids or enteral fluids from one or more containers to a patient. The valve includes a shear-away interference member which holds the valve in a closed position prior to use in order to prevent accidental premature free flow of fluid therethrough. The valve also includes a venting passage for allowing access of sterilization gas into all fluid flow passages of the valve even when the valve stem is rotated to a closed position.

15 Claims, 7 Drawing Sheets

STOP-COCK VALVE

BACKGROUND OF THE INVENTION

1. Field of the Invention

This invention relates generally to stop-cock valves used with fluid delivery sets. More specifically, this invention relates to a stop-cock valve having an improved anti-free flow design which can be sterilized by gas sterilization methods.

2. Description of the Prior Art

It is well known in the prior art to introduce fluids to a patient, either intravenously or enterally for the purposes of medication or alimentation. Such fluid delivery systems typically include one or more flexible plastic tubes connected to one or more containers of fluid to be administered to the patient. In many instances, it is desirable to switch from one fluid container to another during patient administration either for purposes of changing the fluid being administered, or to flush the fluid delivery set to prevent blockage of the fluid line from occurring during use. To accommodate the delivery of fluid from a plurality of containers to a patient, it is well known to provide the fluid delivery set with a stop-cock valve which allows switching from one fluid container to another. Such valves normally employ a rotatable stem which allows the operator thereof to choose which fluid container is placed in fluid flow communication with the patient by rotation of the stem relative to the valve.

One of the primary difficulties with this type of valve is that it is not always apparent to the operator which fluid flow container is in fluid flow communication with the patient. Also, in the particular instance where the operator is preparing the fluid delivery set for initial use with a patient, it is often difficult to ensure that the valve has remained closed in order to prevent accidental premature free-flow of fluid during preparation of the delivery set. Another common difficulty with stop-cock valves of this type is that of ensuring that complete sterilization of the fluid flow channels within the rotating stem thereof occurs during gas sterilization. Since an open gas flow passage must be available through the stem in order to ensure proper gas sterilization of the internal flow passages therethrough, it is necessary to be able to ensure that the rotating stem is always in the proper position to allow free-flow of gas therethrough when the valve is being sterilized.

Accordingly, there is a need in the prior art to develop a stop-cock type valve which allows for simple and immediate visual and/or tactile indication of the position of the rotatable stem in the valve. Further, there is a need in the art for a stop-cock valve which ensures that the rotatable stem thereof remains in the closed position prior to initial use in order to avoid accidental free flow of fluid therethrough during setup. Also there is a need in the art for a stop-cock valve which is gas sterilizeable with complete assurance that the sterilizing gas has access to the flow passages within the rotating stem. There is also a need for a valve which never allows fluid flow connection to occur between inlet ports, regardless of the position of the valve stem thereof so as to prevent intermixing of solutions in the fluid containers which may be attached to the inlet ports.

OBJECTS AND SUMMARY OF THE INVENTION

It is therefore an object of the present invention to provide a stop-cock valve usable with a fluid delivery set which readily indicates to the operator thereof the fluid flow position of the valve's rotating stem.

It is another object of the present invention to provide a stop-cock valve which is maintained in a closed position prior to initial use.

It is further an object of the present invention to provide a stop-cock valve which can be gas sterilized with assurance that sterilization of the fluid flow passages within the rotatable stem thereof will be subjected to the sterilization gas.

These and other objects of the present invention are realized in a presently preferred embodiment of a stop-cock valve, shown and described for purposes of illustration and not by way of limitation, intended for use in conjunction with a fluid delivery set for delivering enteral feeding fluid to a patient. The valve includes a valve body having at least one inlet port therein adapted to be attached through tubing to a fluid container and at least one outlet port adapted to be attached through tubing to a patient, a rotatable valve stem formed with fluid flow passages which are positioned to interconnect with the inlet and outlet ports in the valve body upon rotation thereof, and a valve handle integrally formed with the stem usable by the operator for rotating the stem to the desired position. The handle is uniquely shaped to give tactile and visual input to the operator as to its position relative to the valve body and the open fluid flow path through the valve.

The invention also includes a shear-away interference member which interferes with initial attempted rotation of the rotatable stem relative to the valve body to prevent accidental premature rotation of the stem prior to its intended initial use so that premature free flow of fluid through the valve cannot occur. The shear-away interference member can be overcome by the operator upon the operator's initial intentional rotation of the valve stem by exertion of an elevated rotational force which operates to destroy the interference member which thereafter does not inhibit rotation of the rotatable stem.

The invention also includes a sterilization passage which connects one of the ports of the valve body directly with the fluid flow passages within the rotatable stem whenever the rotatable stem is in its completely closed position. In this manner, a newly assembled valve having its valve stem in the initial completely closed position (the stem being held in its initial closed position by the shear-away interference member) can be gas sterilized with complete assurance that the sterilizing gas will have access to the fluid flow passages within the rotatable stem for proper sterilization while at the same time ensure that fluid flow through the valve is prevented.

BRIEF DESCRIPTION OF THE DRAWINGS

The above objects and advantages of the present invention will become apparent from the following more detailed description, when taken in conjunction with the accompanying drawings in which like elements are identified with like numerals throughout, and in which.

DETAILED DESCRIPTION OF THE PREFERRED EMBODIMENTS

As shown in the exemplary drawings for the purposes of illustration, an embodiment of a stop-cock valve made in accordance with the principles of the present invention, referred to generally by the reference numeral 10, is provided for regulating fluid flow through a fluid delivery set such as may be designed for enteral feeding of a patient.

Figure 1:
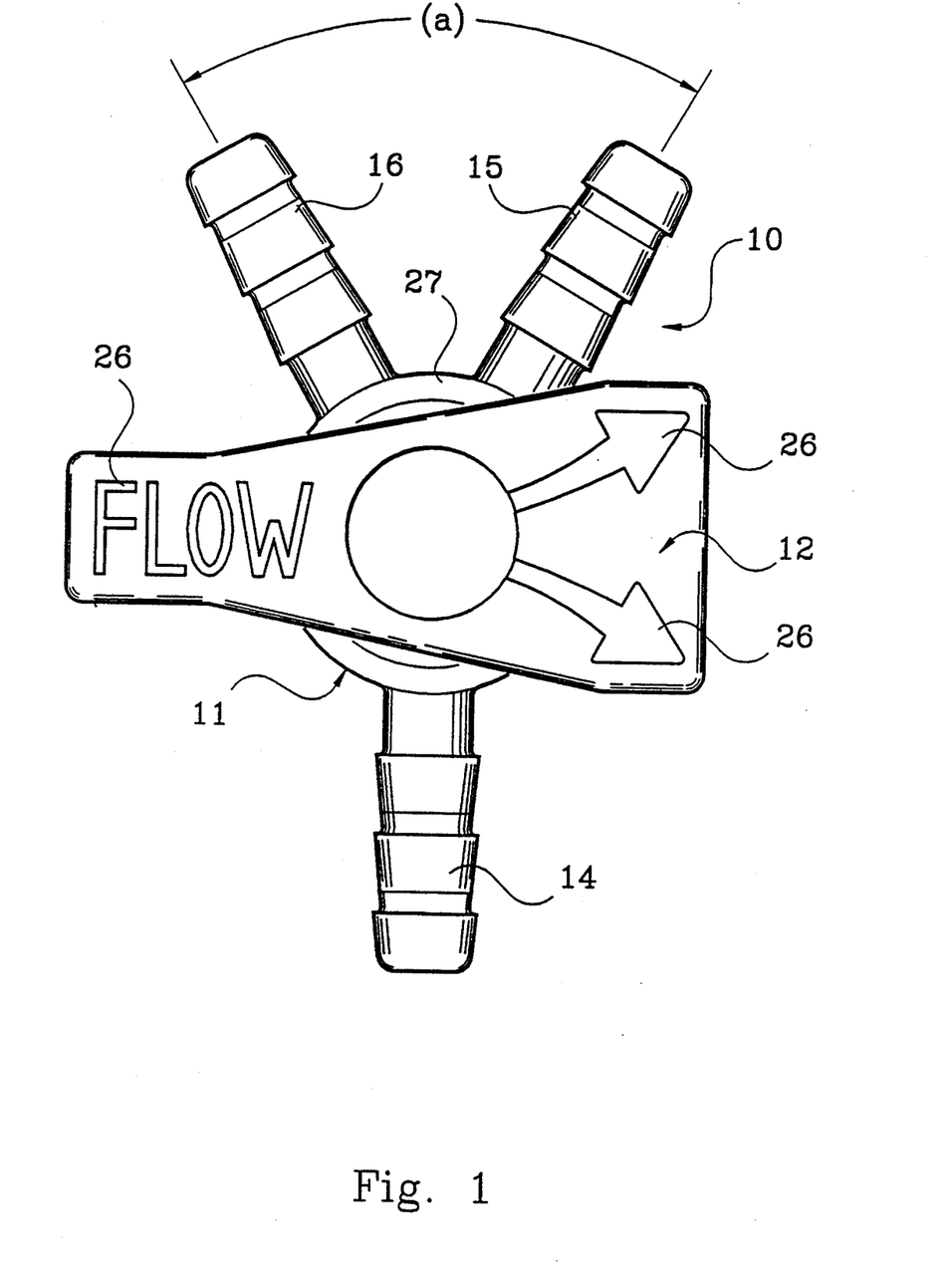
FIG. 1 is a top plan view of a preferred embodiment of a stop-cock valve made in accordance with the principles of the present invention.
Figure 2:
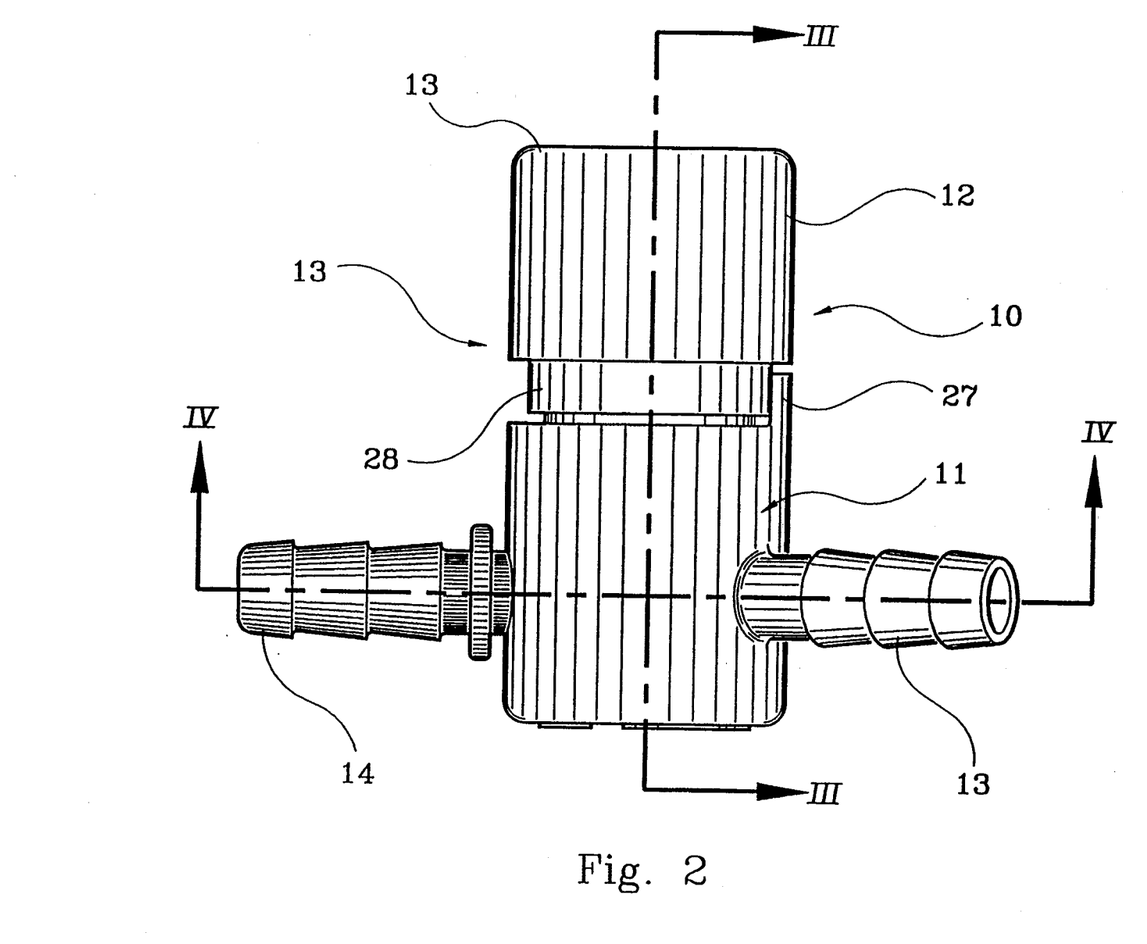
FIG. 2 is a side view of the preferred embodiment of the valve of the present invention.
Figure 3:
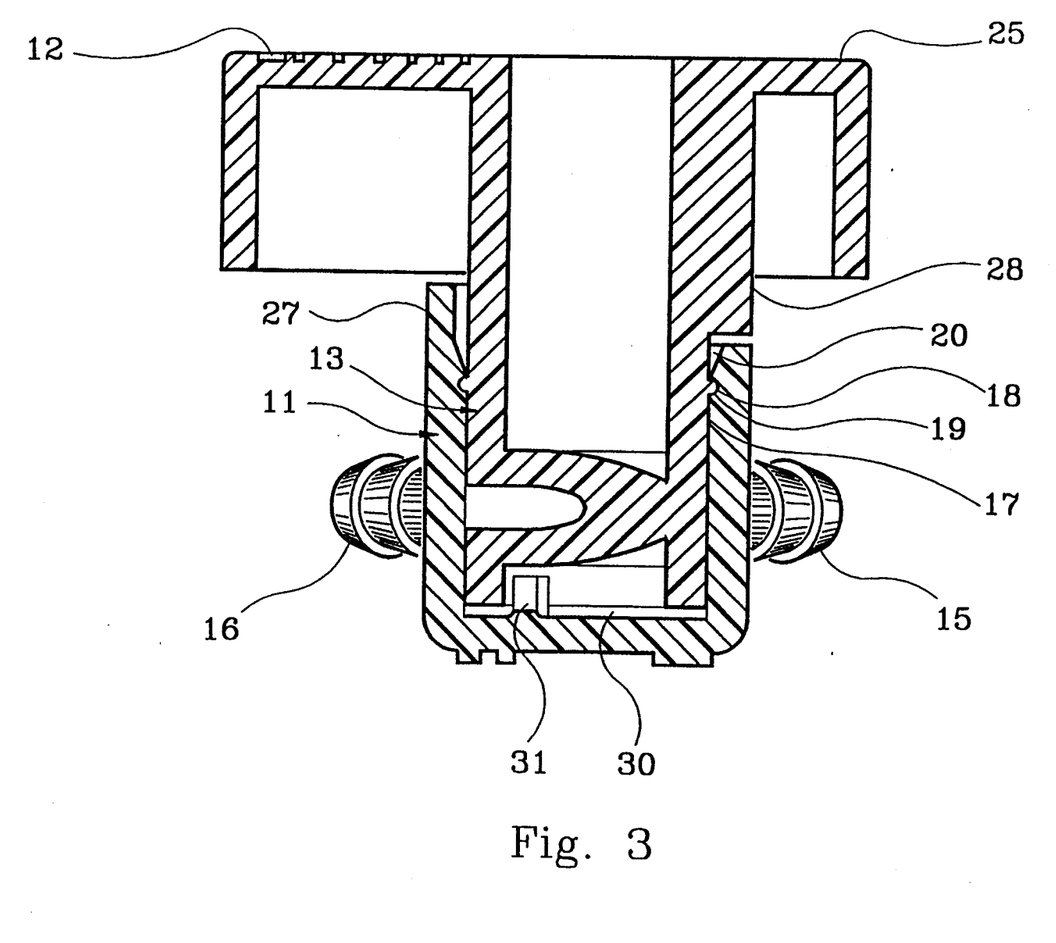
FIG. 3 is a cross-sectional view of the preferred embodiment of the present invention taken along line III—III of FIG. 2.

More specifically, as shown in FIGS. 1-3, valve 10 includes a valve body 11 and a handle 12. The handle 12 is integrally formed with a rotatable stem 13 which is held within a cavity 17 of the body 11 by the snap fit attachment of an annular rib 18 of the stem 13 into an annular detent 19 adjacent the open end of the body cavity 17. A slightly beveled entrance section 20 in the body cavity 17 assists in forming the snap fit between the stem 13 and the body 11.

The body 11 includes a male outlet port 14 and a pair of male inlet ports 15 and 16 which are designed to be attachable to tubular members in a well known manner to place the valve in fluid flow connection with one or more fluid containers (not shown) and a patient to whom the fluid is to be delivered. Each of the ports 14, 15 and 16 lie in a single plane, and each includes a longitudinal axis which intersect at the center of the body cavity 17 and which are perpendicular to the longitudinal axis about which the body 11 and stem 13 rotate relative to each other. The longitudinal axes of the male inlet ports 15 and 16 form an included angle (a) of 60°, and the axis of the male outlet port 14 is equidistant (150°) from both inlet ports 15 and 16.

Figure 4:
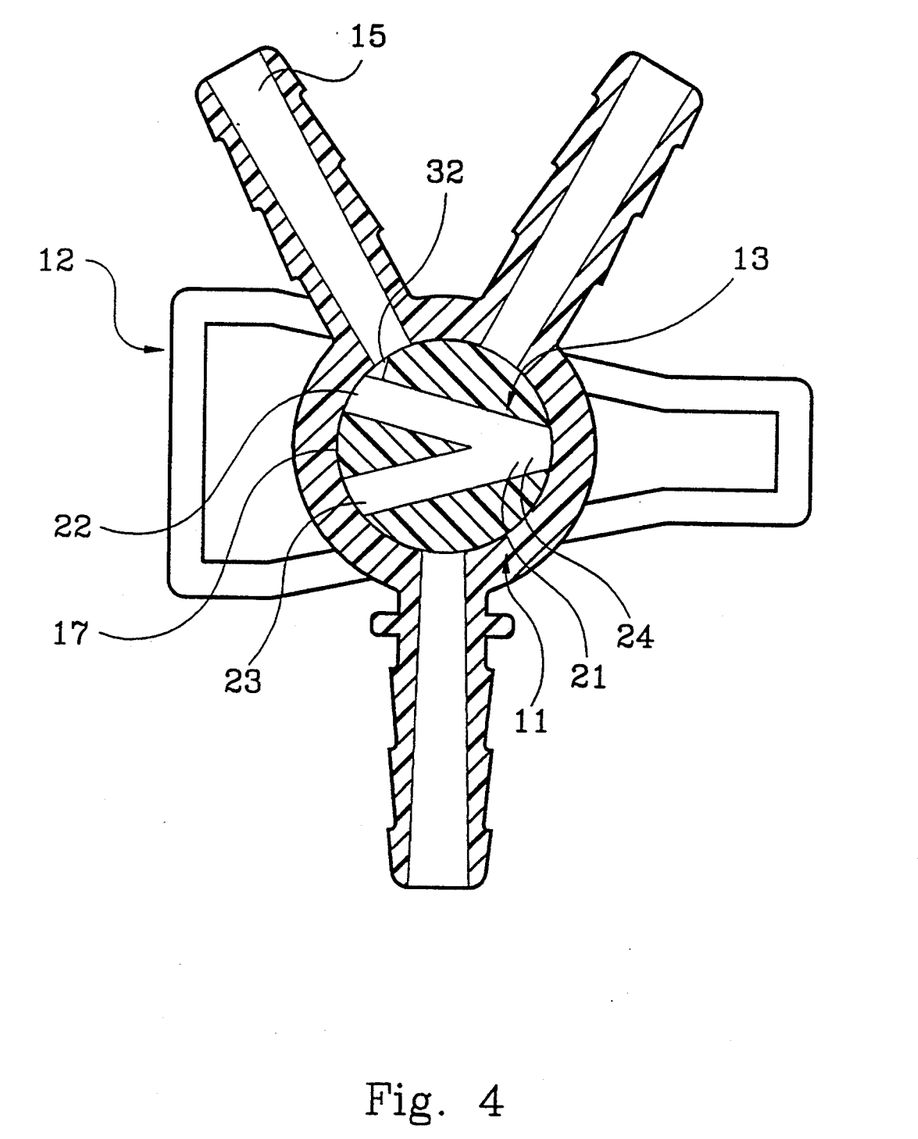
FIG. 4 is a cross-sectional view of the preferred embodiment of the present invention taken along line IV—IV of FIG. 2 showing the valve stem thereof in the closed position.
Figure 5:
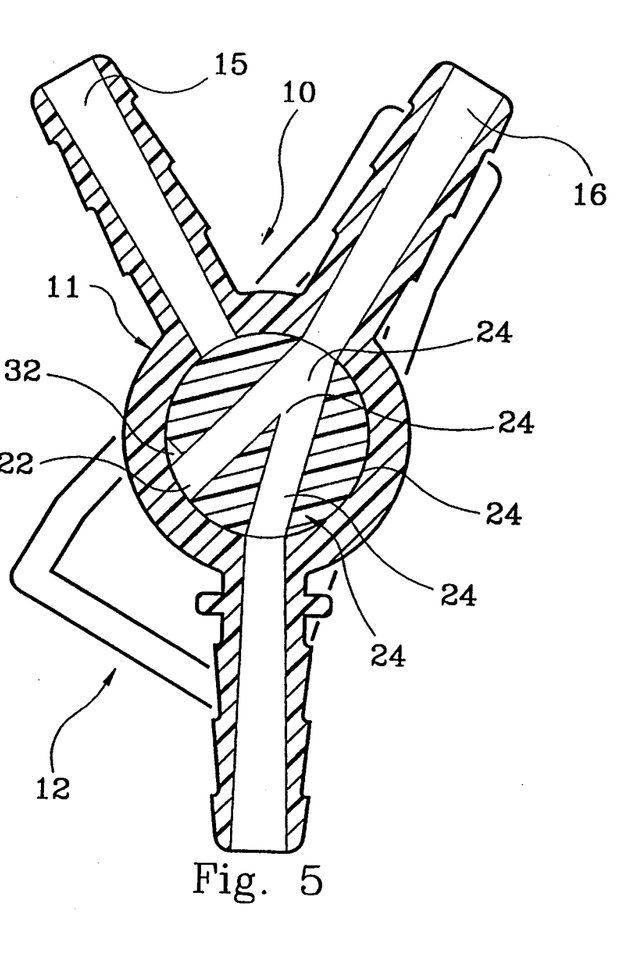
FIG. 5 is a cross-sectional view similar to FIG. 4 except that the valve stem is rotated 60° to a first open position.
Figure 6:
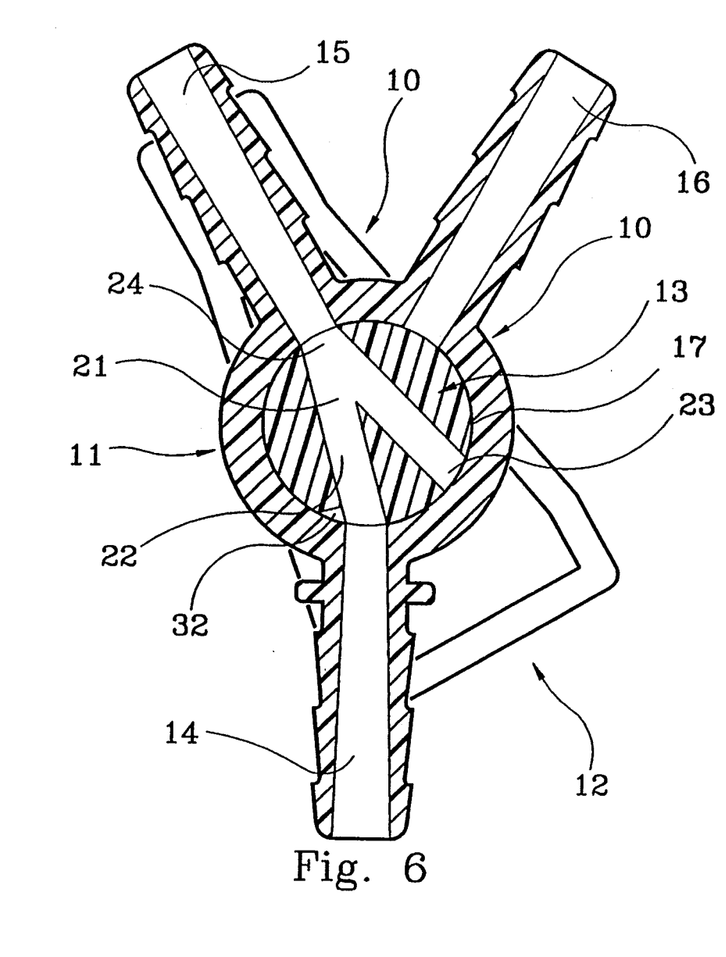
FIG. 6 is a cross-sectional view similar to FIG. 4 with the valve stem rotated 120° to a second open position.

As shown in FIGS. 4-6, the rotatable stem 13 preferably includes a V-shaped or Y-shaped fluid flow passage 21 comprising a first arm 22 and a second arm 23 which have a convergence at 24. The preferred embodiment of valve 10 incorporates at least three operational positions of the rotatable stem 13 relative to the body 11. A first or "closed" operating position is shown in FIG. 1 and FIG. 4. As can be seen, all outlets of the fluid flow passage 21 through the stem 13 are positioned adjacent the body cavity 17 of the body 11. As is clearly evident, in this position, the rotatable stem 13 prevents fluid flow from either inlet port 15 or 16 from passing therethrough into the outlet port 14.

As shown in FIG. 1, the top surface 25 of the handle 12 includes markings 26 which may be in the form of words and/or directional arrows which indicate the direction of flow through the valve 10. As is evident in FIG. 1, the markings 26 indicate that the handle 12 (and similarly the stem 13) is not positioned in any manner such that fluid can flow from either inlet port 15 or 16 to the outlet port 14.

FIG. 5 shows the rotatable stem 13 rotated 60° from its position in FIG. 4. This is the second operating position of the valve 10, and allows fluid flow from inlet port 16 through the second arm 23 of the fluid flow passage 21 into the outlet port 14.

FIG. 6 shows the rotatable stem 13 rotated a distance of 60° from its position shown in FIG. 5. This is the third operational position of the valve 10 which allows fluid flow from inlet port 15 through the first arm 22 of the fluid flow passage 21 into the outlet port 14.

As can be seen in FIGS. 4-6, rotation of the stem 13 through an included angle of only 120°, moves the stem 13 through all possible operating positions of use, i.e., closed, flow from inlet port 16 to outlet port 14, and flow from inlet port 15 to outlet port 14. Each of the three operational positions are equidistantly spaced at a rotational angle of 60°. It should also be well noted that there are no positions of the valve stem 13 in which flow through the valve 10 can occur except the 60° and 120° (second and third) operational positions.

Referring to FIG. 3, it can be seen that the shoulder 27 on the body 11 interferes with the shoulder 28 on the stem 13 to prevent relative rotation of the body 11 and stem 13 outside of the above described 120° angle.

Figure 7:
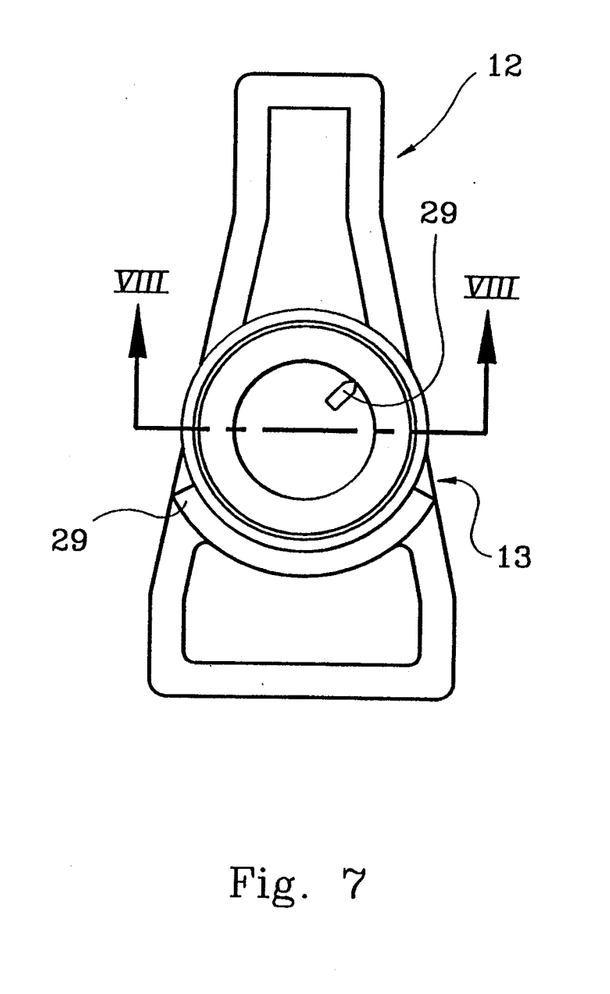
FIG. 7 is a bottom view of the valve stem of the preferred embodiment of the present invention showing the shear-away interference member thereon.
Figure 8:
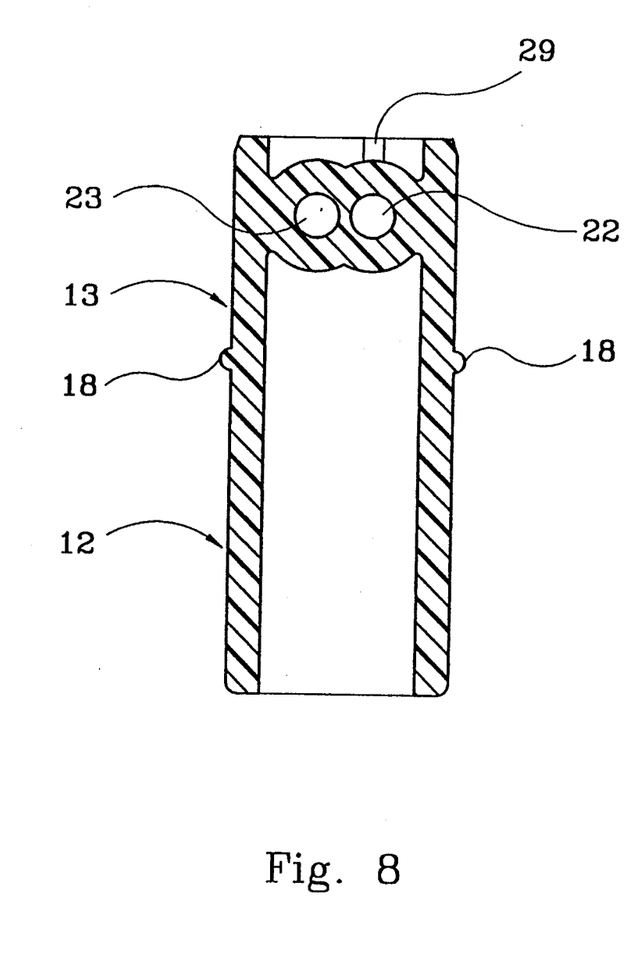
FIG. 8 is a cross-sectional view of the preferred embodiment of the valve stem of the present invention taken along line VIII—VIII of FIG. 7.

As shown in FIGS. 7-8, the rotatable stem 13 may include a shear-away interference member 29 positioned below the fluid flow passage 21. When the rotatable stem 13 is positioned within the body cavity 17 of the body 11, the shear-away interference member 29 is positioned adjacent the bottom surface 30 of the cavity 17. As shown in FIG. 3, a rigid protrusion 31 may also be integrally formed with the body 11 to extend above the bottom surface 30 of the cavity 17 so as to be located in an interference position with the shear-away interference member 29. When the valve is assembled by inserting the rotatable stem 13 into the body cavity 17, it is intentionally inserted with the rotatable stem 13 in the "closed" position relative to the body 11 (as shown in FIGS. 1 and 4). In this initial position, the shear-away interference member 29 is positioned relative to the rigid protrusion 31 so as to be interfering with relative rotation of the stem 13 and the body 11. The shear-away interference member 29 is positioned so that the initial rotation of the stem 13 from the "closed" position cannot be accomplished without intentionally shearing the shear-away interference member 29 away from the stem 13 with the rigid protrusion 31. Shearing of the shear-away interference member 29 requires a significantly higher rotational force to be exerted on the stem 13 before initial rotation out of the "closed" position can occur. In this manner, the shear-away interference member 29 substantially inhibits accidental initial rotation of the stem 13 and thereby ensures that the valve 10 remains in its original "closed" position at all times subsequent to its initial assembly, even through sterilization, packaging, and setup procedures, until first use of the valve 10 as a part of a fluid delivery set occurs.

As is readily apparent, the positions of the shear-away member 29 and the rigid protrusion 31 may be reversed on the stem 13 and body bottom surface 30 if desired with substantially the same operative result.

Figure 9:
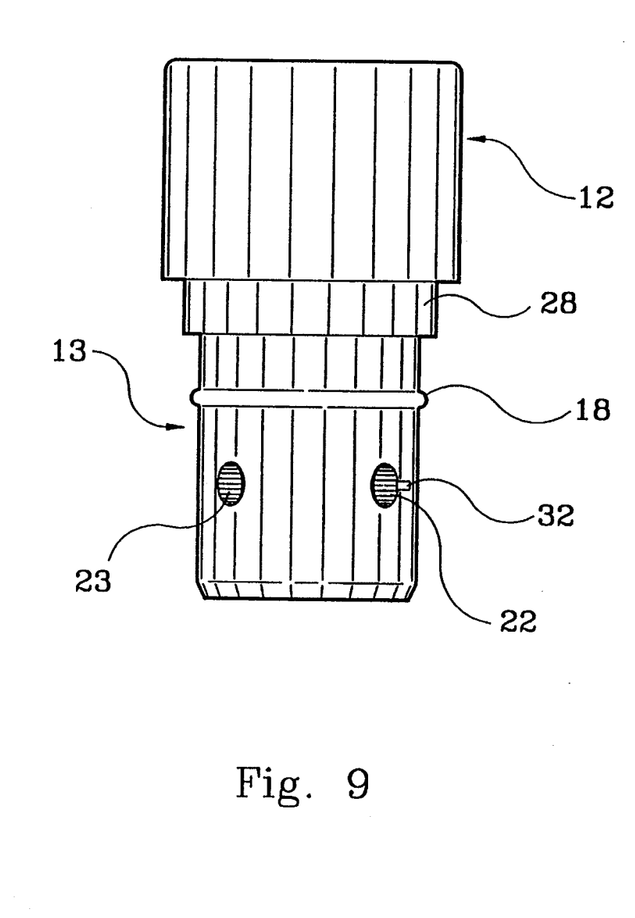
FIG. 9 is a side view of the preferred embodiment of the valve stem of the present invention showing the sterilization passage thereof.

Referring now to FIGS. 4 and 9, a sterilization passage 32 is also positioned in the rotatable stem 13 so that fluid flow communication can exist between the fluid flow passage 21 and the inlet port 15 to assist in sterilization of the valve 10. When the rotatable stem 13 and body 11 are in the "closed" position as shown in FIG. 4, the sterilization passage 32 allows sterilization gas to pass through inlet port 15 into the fluid flow passage 21 to ensure complete sterilization of the valve 10.

Figure 10:
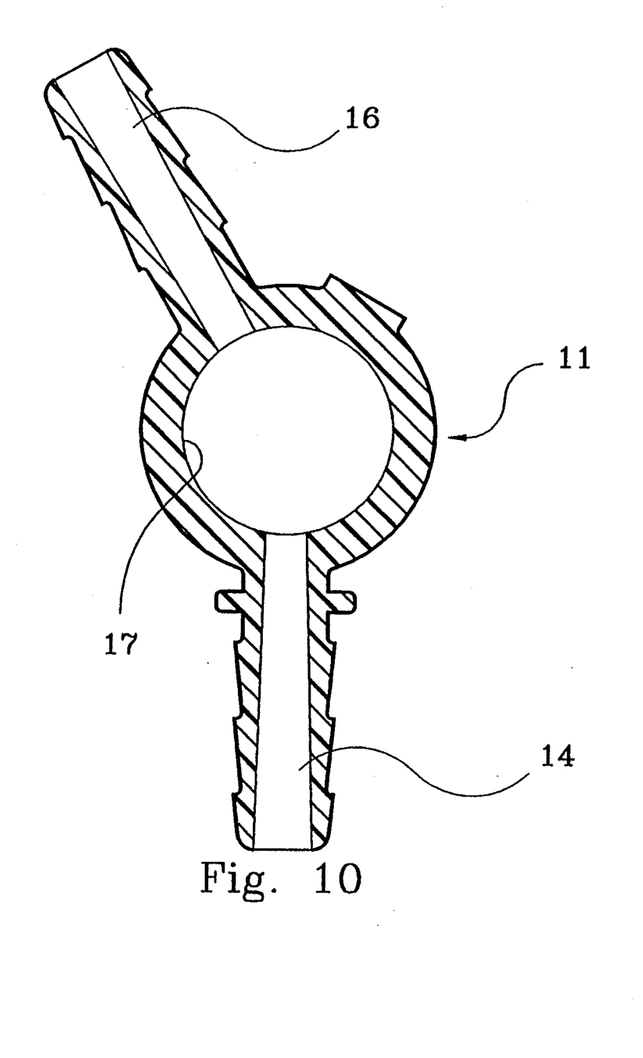
FIG. 10 is a cross-sectional view of a second preferred embodiment of the invention showing the valve body thereof including only a single inlet port.

As shown in FIG. 10, a second preferred embodiment of the valve 10 of the present invention may include a valve body 11' which has only one inlet port 15. The valve body 11' as shown in FIG. 10 operates in an identical manner as the body 11 as shown in FIGS. 1–9 except that of course no flow through the valve 10 occurs until the rotatable stem 13 is rotated to place fluid flow passage 21 in fluid flow alignment with the single open inlet port 15. It should be noted that although the valve body 11' shown in FIG. 10 is modified to include only one inlet port 15, the rotatable stem 13 may nevertheless be constructed in an identical manner as described above with respect to the first preferred embodiment of the invention as shown in FIGS. 19. It should also be noted that either inlet port 15 or 16 may be formed as the single inlet port of the second preferred embodiment of the valve 10. The invention is not intended to be limited to a single position of the inlet port, even though only inlet port 15 is shown in FIG. 10.

It will be apparent from the foregoing that, while particular embodiments of the invention have been illustrated and described, various modifications can be made thereto without departing from the spirit and scope of the invention. Accordingly, it is not intended that the invention be limited, except as by the appended claims.

We claim:

1. A valve comprising:
   a valve body having at least one inlet port and at least one outlet port;
   a valve stem positioned at least partially within said valve body and including a handle, said valve stem including at least one fluid flow passage therethrough, said valve stem being rotatable relative to said valve body between a first position in which fluid flow between said at least one inlet port and said at least one outlet port is prevented, and a second position in which said at least one fluid flow passage connects said at least one inlet port with said at least one outlet port for fluid flow therethrough; and
   rotation interference members for substantially inhibiting initial relative rotation between said valve stem and said valve body between said first position and said second position, said rotation interference members including a rigid protrusion extending either from said valve body or said valve stem and a shear-away interference member extending from the other of said valve body or said valve stem, said rigid protrusion and said shear-away interference member being positioned on said valve body and said valve stem such that said shear-away interference member and said rigid protrusion contact each other and interfere with initial rotation of said valve stem relative to said valve body between said first position and said second position,
   whereby, said shear-away interference member is removed from its attachment with said valve body or said valve stem by said rigid protrusion when rotational force exerted on said valve relative to said valve body to move said valve stem from said first position to said second position exceeds a predetermined value.

2. A valve according to claim 1 wherein said predetermined force value required to detach said shear-away interference member during initial movement of said valve stem relative to said valve body from said first position to said second position is significantly greater than the value of rotational force required to subsequently move said valve stem relative to said valve body from said first position to said second position after said shear-away interference member has been detached.

3. A valve according to claim 1 wherein said at least one fluid flow passage through said valve stem includes a V-shaped fluid flow passage having a first arm and a second arm which converge into a single fluid flow path.

4. A valve according to claim 1 wherein said at least one inlet port includes two inlet ports, said two inlet ports and said at least one outlet port lying in a single plane.

5. A valve according to claim 1 wherein said valve body and said valve stem include shoulder members which allow rotation of said valve body relative to said valve stem through an angle of only 120° or less.

6. A valve according to claim 1 wherein said handle includes indicia formed thereon for marking the path of fluid flow through said valve.

7. A valve according to claim 1 further including
   at least one vent passage formed in said valve stem such that said at least one inlet port and said at least one fluid flow passage are in fluid flow communication when said valve stem is in said first position relative to said valve body.

8. A valve according to claim 7 wherein said at least one fluid flow passage through said valve stem includes a V-shaped fluid flow passage having a first arm and a second arm which converge into a single fluid flow path.

9. A valve according to claim 7 wherein said at least one inlet port includes two inlet ports, said two inlet ports and said at least one outlet port lying in a single plane and said two inlet ports being rotationally spaced from each other at an angle of 60°.

10. A valve according to claim 7 wherein said valve body includes a body shoulder member and said valve stem includes a stem shoulder member which cooperate to prevent rotation of said valve body relative to said valve stem through an angle of more than approximately 120°.

11. A valve according to claim 7 wherein said handle includes indicia formed thereon for marking the path of fluid flow through said valve.

12. A valve comprising:
    a valve body having at least two inlet ports and at least one outlet port;

a valve stem positioned at least partially within said valve body and including a handle, said valve stem including a fluid flow passage having a first arm and a second arm which converge into a single fluid flow path, said valve stem being rotatable relative to said valve body between a first position in which fluid flow between said at least two inlet ports and said at least one outlet port is prevented, a second position in which said first arm of said fluid flow passage connects one of said at least two inlet ports with said at least one outlet port for fluid flow therethrough, and a third position in which said second arm of said fluid flow passage connects the other of said at least two inlet ports with said at least one outlet port for fluid flow therethrough; and shoulder members on said valve body and said value stem for preventing relative rotation of said valve stem and said valve body except between said first, second, and third positions, whereby, rotation of said valve stem relative to said valve body to allow fluid flow connection between said one of said at least two inlet ports and said other of said at least two inlet ports is prevented.

13. A valve according to claim 12 wherein said at least two inlet ports and said at least one outlet port lie in a single plane.

14. A valve according to claim 12 wherein said shoulder members allow rotation of said valve body relative to said valve stem through an angle of only 120° or less.

15. A valve according to claim 12 wherein said handle includes indicia formed thereon for marking the path of fluid flow through said valve.

* * * * *